United States Patent [19]

Hutchins

[11] 4,117,115

[45] Sep. 26, 1978

[54] TREATMENT OF CONJUNCTIVITIS WITH POWDERED ALUMINUM

[76] Inventor: Frank Hutchins, P.O. Box 9035, 67 Pinedale Rd., Asheville, N.C. 28805

[21] Appl. No.: 840,141

[22] Filed: Oct. 7, 1977

Related U.S. Application Data

[62] Division of Ser. No. 771,645, Feb. 24, 1977.

[51] Int. Cl.² .................... A61K 33/22; A61K 33/06
[52] U.S. Cl. ..................................... 424/148; 424/154
[58] Field of Search ................................ 424/148, 154

[56] References Cited

U.S. PATENT DOCUMENTS

| | | | |
|---|---|---|---|
| 3,035,971 | 5/1962 | Anderson | 424/148 |
| 3,098,790 | 7/1963 | Mettentleiter | 424/154 |

OTHER PUBLICATIONS

The Merck Veterinary Manual, 3rd ed., Merck & Co., pp. 213 & 214 (1967).

The Merck Index, 9th ed., Merck & Co., pp. 311 and 325 (1976).

*Primary Examiner*—Albert T. Meyers
*Assistant Examiner*—D. W. Robinson
*Attorney, Agent, or Firm*—Berman, Aisenberg & Platt

[57] ABSTRACT

Powdered aluminum aids in the treatment of, the alleviation of suffering during and the relief from conjunctivitis. When administered to the eye of an animal afflicted with croupous or membranous conjunctivitis, powdered aluminum assists in breaking down and removing the milky film associated with this malady. The powdered aluminum may be applied to a diseased eye by direct application, by spray or by an eye protector which may be tinted to further assist in the treatment of conjunctivitis by shutting out sun's and other light rays from the afflicted eye.

The powdered aluminum is administered as such or in admixture with boric acid and/or antibiotic.

16 Claims, 4 Drawing Figures

TREATMENT OF CONJUNCTIVITIS WITH POWDERED ALUMINUM

This is a division of application Ser. No. 771,645, filed Feb. 24, 1977.

BACKGROUND

Conjunctivitis is a generic term relating to inflammation of the conjunctiva. The inflammation can have one or more of numerous causes, such as trauma, infection and allergy, and is in no way limited to afflicting humans. In fact, particular concern with regard to this disorder is in connection with cattle and horses affected thereby.

Sun rays and other actinic radiation are harmful to diseased eyes and impede or prevent curing, healing or obtaining relief from conjunctivitis. It is thus advantageous to block such rays so that they do not reach eyes of subjects afflicted with conjunctivitis.

According to U.S. Pat. No. 3,098,790 powdered aluminum is useful for treating and healing open wounds. Administration by dusting and spraying is also reported in this patent.

SUMMARY OF THE INVENTION

Powdered aluminum assists in treating, obtaining relief from and curing conjunctivitis, particularly membranous or croupous conjunctivitis, but also other forms, such as actinic and acute contageous conjunctivitis. In addition to impeding the passage of sun rays into an eye sprayed or otherwise treated with powdered aluminum, such aluminum, e.g. in micronized form, breaks up and/or removes the white milky film characteristic of membranous or croupous conjunctivitis.

By combining the powdered aluminum with a minor proportion of boric acid, a particularly advantageous composition results. The boric acid cooperates with the powdered aluminum and assists in removing all foreign matter, including the residue of the broken down milky film, from the affected eye to which the composition has been applied. The powdered aluminum appears to act as a cutting agent with regard to the white milky film, which it removes from the eye. When the admixture is sprayed into an eye of an afflicted host, it cuts away the film and is washed from the eye with the film residue by normal tear action.

A minor proportion of an antibiotic is also advantageously combined with the powdered aluminum. Not only does such antibiotic impede or prevent further infection, it acts positively in the treatment of conjunctivitis when the latter is caused or aggravated by a microorganism.

The powdered aluminum, either alone or with boric acid and/or an antibiotic, may be applied to the diseased eye of the animal via an eye protector in the preferred form of a curved lens having an amount of the curing agent predisposed thereon. The lens is preferably tinted to further assist in shielding the afflicted eye from harmful outside radiation. The lens, which may be of any suitable shape so as to cover the eye, also preferably includes means for ventilating the eye, and means for permitting the eye to drain. The ventilating and drainage means, in a preferred form, each are embodied by a wire screen mesh preferably formed at the lower portion of the lens of a rust-proof material. The lens structure also preferably includes means for conveniently mounting same about the afflicted eye. The eye protector may be utilized in treating conjunctivitis either alone or in combination with the powdered aluminum or compounds thereof.

BRIEF DESCRIPTION OF THE DRAWINGS

The features and advantages of the present invention outlined above will become better understood from the following detailed description of the present invention considered partly in connection with the accompanying drawings, in which.

DETAILED DESCRIPTION OF THE INVENTION

Figure 1:
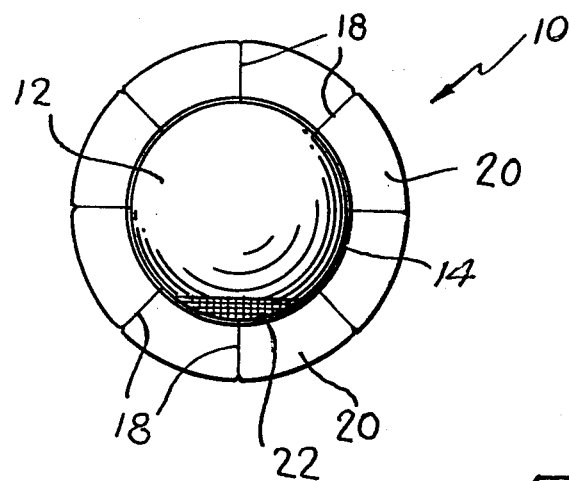
FIG. 1 is a front, plan view of a preferred embodiment of an eye protector/applicator of the present invention.
Figure 2:
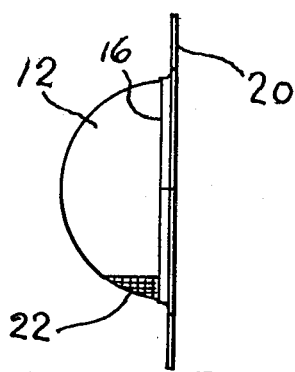
FIG. 2 is a side view of the preferred embodiment illustrated in FIG. 1.
Figure 3:
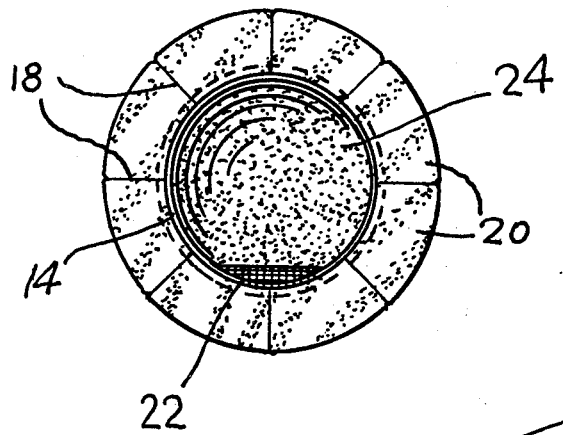
FIG. 3 is a rear, plan view illustrating the preferred embodiment shown in FIG. 1 and having powdered aluminum sprayed thereon.

Aluminum is commercially available in powder form, and such form is suitable for the use contemplated by this invention. The powdered aluminum must naturally be sufficiently sterile or contaminant free to be pharmacologically acceptable for administration to the surface of an eye.

The powdered or pulverized aluminum is of any suitable particle-size range, e.g. of 20 microns or smaller. When it has such a particle-size range, it is regarded as micronized aluminum. It is optionally of any particle-size range suitable for the practice of the invention disclosed in U.S. Pat. No. 3,098,790.

In treating conjunctivitis, powdered aluminum is applied to an eye surface either by itself or in combination with one or more other ingredients. In any resulting compositions the powdered aluminum should be the predominant component. Boric acid is advantageously admixed with the powdered aluminum and works with the powdered aluminum to assist in dispelling broken down white milky film and other foreign matter from the eye. Whenever tissue is inflamed, it is more subject to infection. By incorporating an antibiotic with the powdered aluminum, such infection may be warded off. As infection is also one cause of conjunctivitis, an antibiotic is also useful in treating and curing such conjunctivitis.

Compositions useful for administering to eyes of subjects, e.g. horses and cattle, afflicted with conjunctivitis comprise powdered aluminum predominantly or exclusively. (They are dry compositions which are free from, or at least have no requirement for the presence of, vegetable gum.) Such compositions optionally comprise up to about 20 percent by weight of boric acid and up to about 20 percent by weight of antibiotic, e.g. neomycin. Preferred compositions contain about 10 percent by weight of boric acid and about 10 percent by weight of neomycin; they are in the form of a sprayable powder suitable for spraying directly onto the surface of an affected eye. (Suitable spraying means are known and do not constitute part of this invention.)

The compositions used for this invention need not be administered by spraying onto an eye surface; they are optionally applied, e.g., from a squeeze bottle directly to such surface in amount of from about 1 to 2 milligrams per application per eye. One particularly advantageous mode of treatment employs an animal-eye protector with a lens heavily coated with such a composition, e.g., by spraying the composition on the inside surface of the lens. As the composition is in powder form and the coated lens is so close to the affected eye, the powder intermittently, e.g. as the head of the animal is moved, goes into the eye over an extended period of time. The eye protector has the added advantage of keeping sun rays from the eye and providing a way to administer the composition to the eye without exposing the eye to actinic radiation. Powdered aluminum also absorbs sun rays and thus further assists in this phase of treatment.

Referring now to FIGS. 1 through 4, a preferred embodiment of a suitable eye protector and applicator for the powdered aluminum is indicated generally by reference numeral 10. Eye protector 10 includes a central lens portion 12 which may be made of either glass or plastic. Lens 12 is preferably tinted so as to further assist in screening out the sun's radiation, and other harmful light, to facilitate the healing process. While the lens 12 is illustrated as being a spherical section, any suitable shape will suffice.

Figure 4:
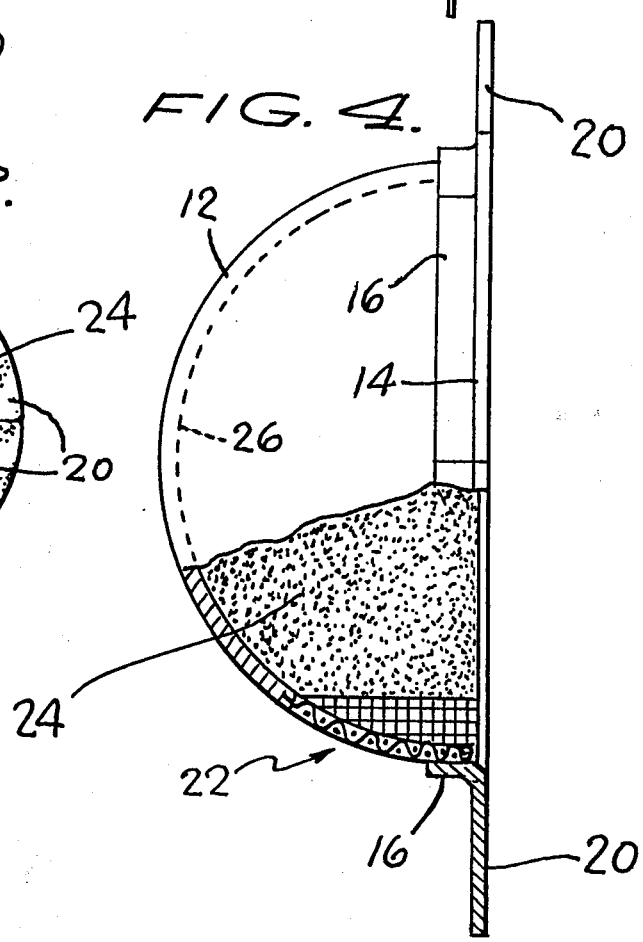
FIG. 4 is an enlarged, side, partially broken and sectional view of the preferred embodiment shown in FIG. 3.

The lens 12 may be mounted in a substantially circular lens holder or base 14 which has a slightly upstanding peripheral flange 16 formed thereabout within which the lens 12 may be secured (FIG. 4). Extending radially from the base 14 are a plurality of tangs or prongs 18 which serve as mounting means over which an adhesive tape 20 or the like may be placed when fitting the eye protector 10 over the afflicted eye of the animal. Adhesive tape 20 is preferably weather-proof to permit outdoor, uninterrupted use. In lieu of adhesive-backed tape, a rapid drying, weather-proof glue may be employed. Other equally suitable mounting means will suggest themselves to persons of ordinary skill.

At the lower portion of lens 12 is positioned a wire screen mesh 22 which is preferably formed of a rust-proof material, such as plastic. The wire screen mesh 22 serves the dual purpose of ventilating the eye to fresh air and serves as an outlet for possible drainage from the eye. Illustrated in FIGS. 3 and 4 and indicated by reference numeral 24 is the pre-coated micronized aluminum which may be heavily applied to the inner surface 26 of the lens 12 prior to mounting of the eye protector 10 over the afflicted eye. As stated above, while many shapes of lens 12 will be suitable, I have found that one which places the apex of the inner surface 26 within ½ to 1 inch from the surface of the afflicted eye to be particularly advantageous. Clearly, the eye protector 10 may be utilized in its uncoated state as an effective radiation shield for facilitating the healing process.

The provided compositions should be administered to affected eyes as soon as possible after the onset of conjunctivitis. With horses and cattle permanent injury can result from delay. The powdered aluminum or powdered aluminum composition is administered to affected eyes (by spray or by direct application) as often as three times during each 24-hour period until the film is completely removed from the eyes and, perhaps, at a slightly-reduced frequency thereafter until inflammation has completely disappeared. From 1 to 2 milligrams of powdered aluminum are applied to the surface of an affected eye during each administration. This treatment is regarded as the quickest way to remove the white milky film which is characteristic of certain conjunctivitis.

For two-component compositions consisting of powdered aluminum and boric acid, the several ingredients are merely blended together until a uniform and substantially homogeneous dry powder admixture is obtained. For admixtures including an antibiotic, the antibiotic, e.g. neomycin, is first thoroughly blended with the aluminum powder (for about 5 minutes with quantities of 10 grams of aluminum powder and 1 gram of neomycin). If boric acid is to be incorporated therein, the boric acid is then thoroughly blended with the obtained admixture until a substantially homogeneous and thoroughly dry three-component blended composition is obtained.

Obviously, numerous modifications and variations of the present invention are possible in light of the above teachings. It is therefore to be understood that within the scope of the appended claims, the invention may be practiced otherwise than as specifically described herein.

What is claimed is:

1. A process for treating conjunctivitis in an animal which comprises topically administering to a diseased eye of the animal afflicted with conjunctivitis an amount of powdered aluminum sufficient to arrest and relieve the affliction.

2. A process according to claim 1 wherein the powdered aluminum is in combination with at least one of boric acid and antibiotic, the relative proportions being from 0 to 2 parts of boric acid and from 0 to 2 parts of antibiotic per each 10 parts of powdered aluminum.

3. A process according to claim 2 wherein the antibiotic is neomycin.

4. A process according to claim 2 wherein the proportions are about 10:1:1.

5. A process according to claim 1 which comprises administering from 1 to 2 milligrams of powdered aluminum to the eye per application.

6. A process according to claim 1 which comprises spraying the powdered aluminum on the eye.

7. A process according to claim 1 wherein the conjunctivitis is membranous or croupous conjunctivitis and the amount of powdered aluminum is sufficient to break down and thus assist in the removal of the membrane or film which is associated with such conjunctivitis.

8. A process according to claim 1 wherein the animal is a horse.

9. A process according to claim 1 wherein the conjunctivitis is membranous or croupous conjunctivitis.

10. A process according to claim 1 wherein the conjunctivitis is actinic conjunctivitis.

11. A process according to claim 1 wherein the conjunctivitis is acute contageous conjunctivitis.

12. A process according to claim 1 for treating conjunctivitis in cattle and which comprises topically applying the powdered aluminum to a diseased eye of an afflicted animal.

13. A therapeutically-acceptable composition useful for treating conjunctivitis in animals which comprises a substantially uniform admixture of powdered aluminum, boric acid and antibiotic, the composition containing up to 2 parts of boric acid and up to 2 parts of an antibiotic for each 10 parts of powdered aluminum.

14. A therapeutically-acceptable composition according to claim 13 which comprises a substantially uniform admixture of powdered aluminum, boric acid and antibiotic in proportions of about 10:1:1.

15. A sprayable composition according to claim 14 in which the antibiotic is neomycin.

16. A composition according to claim 13 which is free from vegetable gum.

* * * * *

UNITED STATES PATENT AND TRADEMARK OFFICE
CERTIFICATE OF CORRECTION

PATENT NO. : 4,117,115
DATED : September 26, 1978
INVENTOR(S) : Frank Hutchins

It is certified that error appears in the above–identified patent and that said Letters Patent are hereby corrected as shown below:

In the title, line 2, "POWDERED" should read --MICRONIZED--.

Signed and Sealed this

Thirteenth Day of March 1979

[SEAL]

Attest:

RUTH C. MASON
Attesting Officer

DONALD W. BANNER
Commissioner of Patents and Trademarks